United States Patent
Hubbard et al.

(10) Patent No.: US 6,283,973 B1
(45) Date of Patent: Sep. 4, 2001

(54) STRENGTH FIXATION DEVICE

(75) Inventors: Eric Hubbard, Modesto; Robert-Jan Enzerink, Tracy, both of CA (US)

(73) Assignee: DePuy Orthopaedics, Inc., Warsaw, IN (US)

(*) Notice: Subject to any disclaimer, the term of this patent is extended or adjusted under 35 U.S.C. 154(b) by 0 days.

(21) Appl. No.: 09/427,598

(22) Filed: Oct. 27, 1999

Related U.S. Application Data

(60) Provisional application No. 60/114,172, filed on Dec. 30, 1998.

(51) Int. Cl.⁷ .............................. A61F 2/28; F16B 35/00
(52) U.S. Cl. ..................... 606/104; 606/73; 623/13.14; 411/393; 411/411
(58) Field of Search .................. 606/53, 72, 73, 606/74, 104; 623/13.11, 13.12, 13.13, 13.14, 13.17, 13.18; 411/378, 411, 393, 395

(56) References Cited

U.S. PATENT DOCUMENTS

| | | |
|---|---|---|
| 4,537,185 | 8/1985 | Stednitz . |
| 4,760,844 | 8/1988 | Kyle . |
| 4,950,270 | 8/1990 | Bowman et al. . |
| 4,950,295 | 8/1990 | Weigum et al. . |
| 5,059,193 | 10/1991 | Kuslich . |
| 5,062,843 | 11/1991 | Mahony, III . |
| 5,084,050 | 1/1992 | Draenert . |
| 5,129,901 | 7/1992 | Decoste . |
| 5,129,906 | 7/1992 | Ross et al. . |
| 5,156,616 * | 10/1992 | Meadows et al. ............ 606/232 |
| 5,201,738 | 4/1993 | Scott et al. . |
| 5,275,601 | 1/1994 | Gogolewski et al. . |
| 5,282,802 | 2/1994 | Mahony, III . |
| 5,354,299 * | 10/1994 | Coleman .......................... 606/73 |
| 5,360,450 | 11/1994 | Giannini . |
| 5,370,662 * | 12/1994 | Stone et al. .................. 606/73 X |
| 5,383,878 | 1/1995 | Roger et al. . |
| 5,425,733 | 6/1995 | Schmieding . |
| 5,431,652 | 7/1995 | Shimamoto et al. . |
| 5,443,509 | 8/1995 | Boucher et al. . |
| 5,454,811 | 10/1995 | Huebner . |
| 5,456,685 | 10/1995 | Huebner . |
| 5,645,547 * | 7/1997 | Coleman .......................... 606/73 |
| 5,688,285 * | 11/1997 | Yamada ...................... 606/73 X |
| 5,728,160 | 3/1998 | Draenert . |
| 5,891,146 | 4/1999 | Simon et al. . |
| 5,961,524 * | 10/1999 | Crombie ........................ 606/104 |
| 6,045,554 * | 4/2000 | Grooms et al. .................. 606/73 |
| 6,123,710 * | 9/2000 | Pinczewski et al. ............. 606/73 |

OTHER PUBLICATIONS

DIALOG Database Search Results Listing of Various Journal Articles with Accompanying Abstracts (Various Dates), 53 pages.*
1998 brochure, "Quadruple Loop Hamstring Graft Surgical Technique with the Phantom™ SofThread™ Interference Screw," Robert E. Hunter, M.D., 8 pages.
Abstract of United Kingdom Patent. No. 2266460, 1 page, Nov. 1993.

* cited by examiner

Primary Examiner—Jeffrey A. Smith
(74) Attorney, Agent, or Firm—Barnes & Thornburg

(57) ABSTRACT

The present invention relates to a screw comprising a screw body including a tip portion having a front face, an end portion having a rear face and being positioned to lie in spaced-apart relation to the tip portion, a threaded portion having a rounded thread extending between the tip portion and the end portion, and a passageway extending the length of the screw body from the front face to the rear face.

24 Claims, 3 Drawing Sheets

US 6,283,973 B1

STRENGTH FIXATION DEVICE

This application claims priority under 35 U.S.C. § 119(e) to U.S. Provisional Application No. 60/114,172, filed Dec. 30, 1998, which is expressly incorporated by reference herein.

BACKGROUND AND SUMMARY OF THE INVENTION

The present invention relates to bone screws, and particularly to interference screws for use in securing a tissue graft within a bone tunnel. More particularly, the present invention relates to a resorbable bone screw which may be used as an interference screw or as a soft tissue anchor screw.

Interference screws are screws which "interfere with" or drive a bone piece against a bone section or soft tissue graft. For example, in ACL surgery interference screws are often used to secure a bone block of a replacement graft within a bone tunnel. Such screws are often used as a wedge between the bone block and a pre-drilled tunnel wall in the tibia or femur in order to force the bone block against an opposite side of the tunnel wall so that bone ingrowth will fuse the bone block in place. In an ACL replacement, a tendon is typically harvested and then pushed or pulled through the tibial tunnel upwardly into the femoral tunnel. An interference screw is placed in the femoral tunnel to hold the upper bone block against the side of that tunnel.

Interference screws may be made from biocompatible metals, such as titanium or stainless steel. Interference screws may also be made from a wide variety of materials which are known to be resorbable into the body or which will promote bone growth in the tunnel to replace the screw. Preferred materials include PLLA or PLA (Poly-L-Lactide Acid) or cortical allograft bone. Other bioabsorbable materials which are eventually absorbed in the body are known and may be used to make interference screws as well. U.S. Pat. No. 5,364,400 to Rego, Jr. et al. showing an INTERFERENCE IMPLANT and U.S. Pat. No. 5,470,334 to Ross et al. showing a BIOABSORBABLE INTERFERENCE BONE FIXATION SCREW are examples of such screws and each are incorporated herein by reference.

In accordance with the present invention, a screw for use with soft tissue grafts is provided which includes a screw body having a tip portion formed to include a front face, an end portion formed to include a rear face, and a threaded portion extending between the tip portion and the end portion. The screw body further includes drive faces formed to define a passageway which extends from the front face of the tip portion to the rear face of the end portion. The drive faces of the passageway are further formed to extend from the front face of the tip portion to the rear face of the end portion. Preferably, the passageway has a polygonal cross-section. In a preferred embodiment, the polygonal cross-section is square.

In preferred embodiments, the polygonal shape of the passageway extends all the way through the screw body along an axial length of the screw body. The threaded portion of the screw body is formed to include a single thread forming thread segments having rounded crests and troughs in order to secure the soft tissue graft to bone, for example, without damaging the soft tissue graft. Preferably, the screw body is formed from a bioabsorbable material.

In further preferred embodiments, a driver is also provided to operate in combination with the screw body. The driver includes a screw-receiving portion and a handle portion positioned to lie in spaced-apart relation to the screw-receiving portion. In a preferred embodiment, the screw-receiving portion includes a body for being received within the passageway of the screw body and a tapered portion for extending beyond the front face of the tip portion of the screw body. The body of the screw-receiving portion is formed to be received through the passageway of the screw body so that drive faces of the body engage drive faces of the screw body and torsional and axial drive forces exerted by the driver are distributed along the entire length L of the screw body through the drive faces of the driver to the drive faces of the screw body. Optionally, the driver is cannulated for use with a guide wire.

Another aspect of this invention is a method of fixing a tissue graft within a bone tunnel. First, a bone tunnel is prepared to accept the graft. Next, the tissue graft is inserted within the tunnel. A screw having an axial passageway with a plurality of driving surfaces extending the entire length of the screw is driven into the bone tunnel by applying force along the entire length of each of the driving surfaces.

Additional features of the invention will become apparent to those skilled in the art upon consideration of the following detailed description of preferred embodiments exemplifying the best mode of carrying out the invention as presently perceived.

BRIEF DESCRIPTION OF THE DRAWINGS

The detailed description particularly refers to the accompanying figures in which.

DETAILED DESCRIPTION OF THE DRAWINGS

Figure 1:
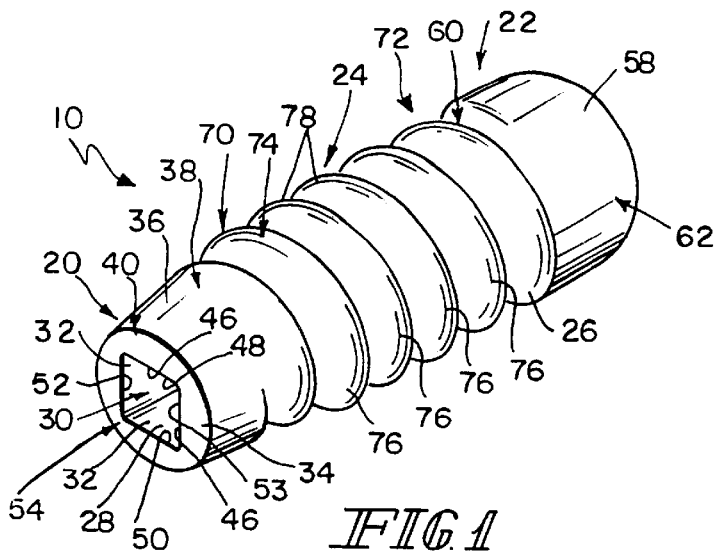
FIG. 1 is a perspective view of the cannulated interference screw of the present invention showing the screw having a screw body including a tapered tip portion, a threaded portion, a rounded end portion, and a square-shaped passageway extending through the screw body.
Figure 7:
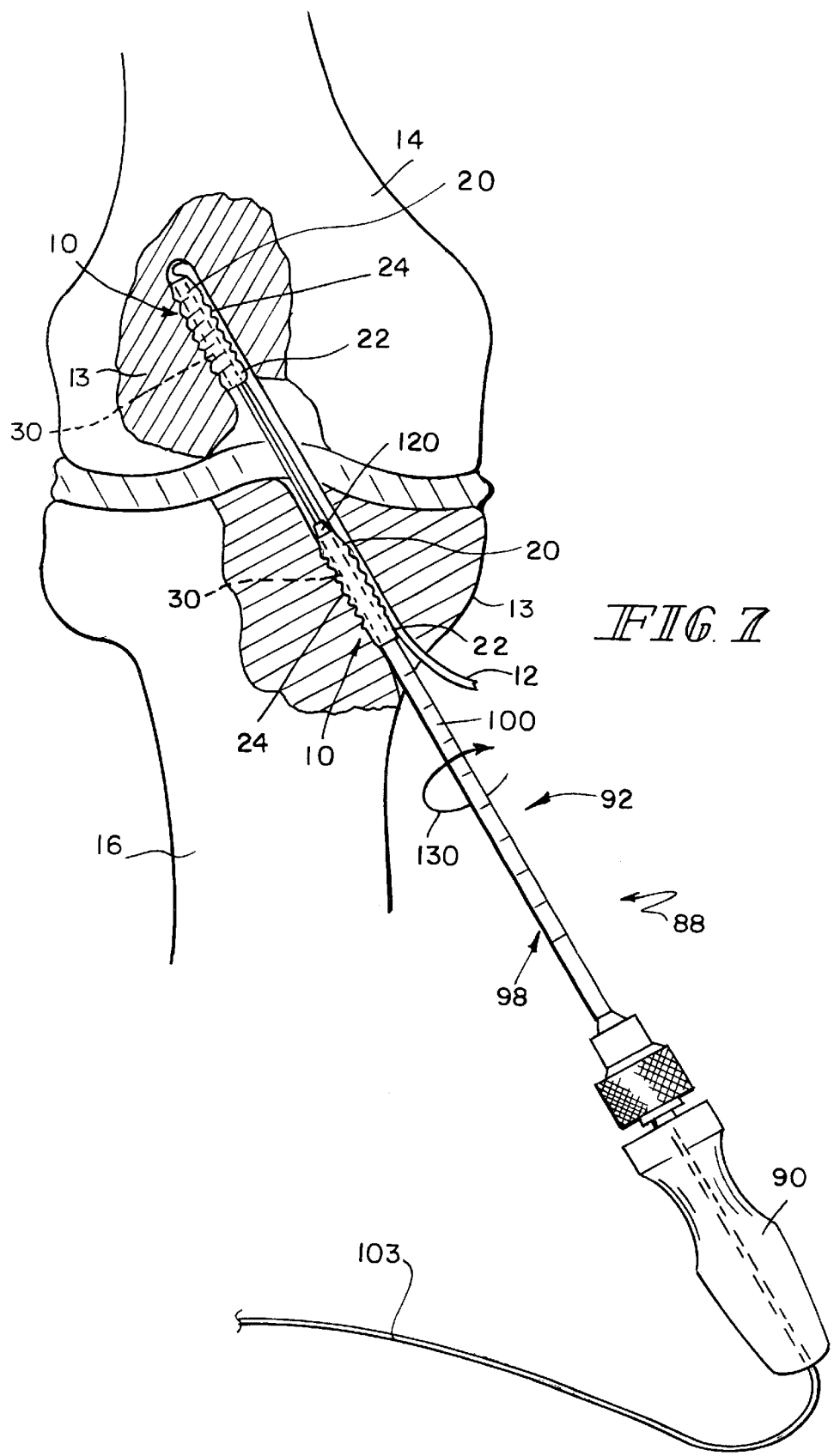
FIG. 7 is a side view of a knee joint in the process of an ACL repair, with portions broken away, showing one screw body positioned to lie within the femoral tunnel in order to wedge between a soft tissue graft and a bone portion of the femur and further showing another screw body mounted on the driver within the tibial tunnel in order to be positioned between another portion of the soft tissue graft and a bone portion of the tibia.

A screw body 10 of FIG. 1 is formed for use with a soft tissue graft 12, as shown in FIG. 7, for example. Screw body 10 is bioabsorbable and is thus is made from material which can be absorbed into the body. Screw body 10 is made to affix soft tissue grafts 12 to bone and is used, for example, in cruciate ligament repairs such as anterior cruciate ligament (ACL) and posterior cruciate ligament (PCL) reconstruction. As shown in FIG. 7, screw body 10 is positioned by a drive tool 88 within a femur 14 to wedge soft tissue graft 12 to a portion of femur 14. Another screw body 10 is positioned within corresponding tibia 16 to wedge the same soft tissue graft 12 to a portion of tibia 16.

Referring now to FIG. 1, screw body 10 is formed to include a tip portion 20, an end portion 22 positioned to lie in spaced-apart relation to tip portion 20, and a threaded portion 24 extending between tip portion 20 and end portion 22. Screw body 10 further includes an outer surface 26 and an inner surface 28 formed to define a passageway 30 therethrough. Finally, screw body 10 includes inner drive faces 32 which extend along an axial length L of screw body 10 and further define passageway 30.

Tip portion 20 is formed to include a front face 34 and a frustoconical wall 36 defining a portion of outer surface 26 of screw body 10. Wall 36 includes a first end 38 coupled to threaded portion 24 of screw body 10 and a second end 40 coupled to front face 34, as shown in FIG. 1. Wall 36 is tapered so that first end 38 has a diameter 42 greater than a diameter 44 of second end 40 (shown in FIG. 2). Front face 34 is circular in shape, however, it is within the scope of the invention to include a front face having various shapes. Front face 34 includes edges 46 which define top edge 48, bottom edge 50, and side edges 52 and 53. Edges 46 form a first opening 54 of passageway 30.

Figure 2:
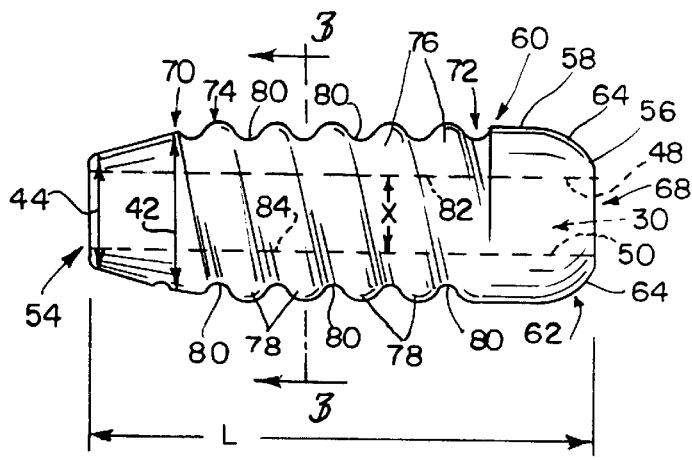
FIG. 2 is a side view of the screw body of FIG. 1 showing (in phantom) the passageway extending through the screw body along an axial length L of the screw body and from a front face of the tip portion to a rear face of the end portion.

As best seen in FIGS. 1 and 2, end portion 22 is formed to include a rear face 56 and a cylindrical wall 58 defining a portion of outer surface 26 of screw body 10. Wall 58 of end portion 22 includes a first end 60 coupled to threaded portion 24 and a second end 62 coupled to rear face 56, as shown in FIG. 1. Wall 58 further includes chamfered edges 64 adjacent to rear face 56, best seen in FIG. 2. Rear face 56 is circular in shape similar to front face 34. It is, however, within the scope of the invention to include a rear face having various shapes. Rear face 56 includes edges 66, as shown in phantom in FIG. 6, similar to edges 46 of front face 34. Edges 66 of rear face 56 form a second opening 68 of passageway 30.

Threaded portion 24 is formed to include a first end 70 coupled to first end 38 of tip portion 20, a second end 72 coupled to first end 60 of end portion 22, and a single thread 74 extending there between. Thread 74 includes multiple thread segments 76, as shown in FIGS. 1 and 2. As illustrated, threaded portion 24 includes five thread segments 76. However, it is understood that it is within the scope of the disclosure to include a threaded portion having any number of thread segments 76 thereon. Also, while illustrated, thread 74 is a single thread. However, a screw body having multiple threads is within the scope of this invention. Thread segments 76 form crests 78 and troughs 80 of single thread 74 so that each thread segment includes a crest 78 and a trough 80 positioned to lie on either side of crest 78, as shown in FIG. 2.

Screw body 10, as mentioned above, is formed for use with soft tissue grafts 12. Specifically, threaded portion 24 of screw body 10 is formed to affix soft tissue grafts 12 to bone 13, as shown in FIG. 7. In the illustrated embodiment, thread segments 76 of threaded portion 24 are large and each crest 78 is rounded in order to engage bone 13 while not damaging soft tissue graft 12. Thread segments 76 are further designed to resist pullout equally in both anterograde and retrograde axial directions.

Figure 3:
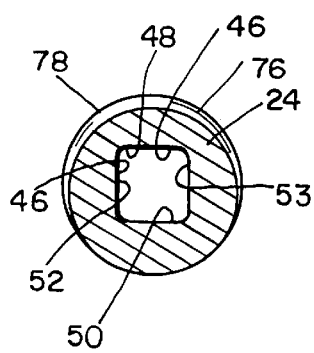
FIG. 3 is a cross-section taken along line 3—3 of FIG. 2 showing the passageway of the screw defined by four edges of equal length formed to provide the square shape of the passageway.

Referring now to FIGS. 2 and 3, first and second openings 54, 68 of passageway 30 are square-shaped and passageway 30 has a square-shaped cross-section. It is within the scope of the disclosure, though, to include a cross section of a wide variety of shapes which provide multiple drive surfaces, for example other polygons. It is further within the scope of the disclosure to include cross-sections having one continuous drive surface such as an ellipse, for example.

A distance X exists between top edge 48, which defines a top inner drive face 82 and bottom edge 50, which defines a bottom inner drive face 84. In the illustrative embodiment, distance X between top and bottom inner drive faces 82, 84 is constant along length L of passageway 30, as shown in FIG. 2. Further, a distance Y exists between side edges 52, 53 and side inner drive faces 86 so that distance Y is constant along length L of passageway 30. In the present application, distance X is equal to distance Y in order to provide passageway 30 having a square-shaped cross-section. In other words, square passageway 30 extends through the entire screw body 10. In a preferred embodiment of a 7×25 mm screw, screw body 10 is formed so that a minimum distance (not shown) between an outer corner of square-shaped passageway 30 and any one of the troughs 80 is 0.0348 inches. However, other configurations are within the scope of the disclosure.

Figure 4:
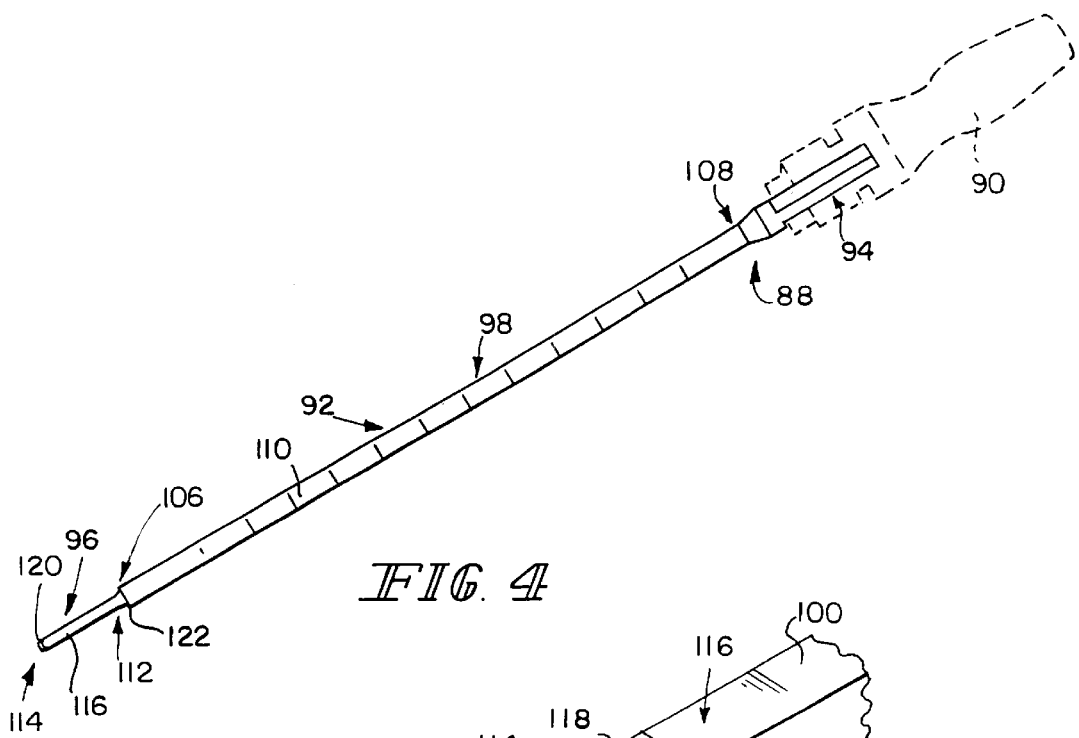
FIG. 4 is a side view of a drive tool for use in combination with the screw body in order to drill the screw body into a femur, for example, including a driver of the present invention and a handle (shown in phantom) and showing the driver including a handle portion to be coupled to the handle, an elongated shaft, and a screw-receiving portion coupled to the shaft, spaced-apart from the handle portion, and formed to receive the screw body thereon for use during ACL surgery, for example.
Figure 5:
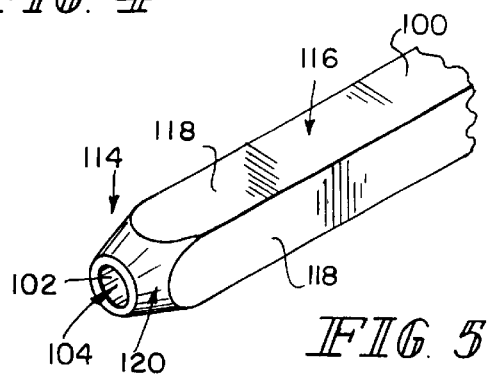
FIG. 5 is a perspective view of the screw-receiving portion of the drive tool of FIG. 4, with portions broken away, showing the screw-receiving portion including a tapered portion and a body having outer drive faces and further showing a portion of a passageway of the driver formed to extend through the driver and receive a guidewire in order to align the driver and screw body combination during surgery.

Screw body 10 is inserted into femur 14 and tibia 16 through the use of a drive tool 88, shown in FIGS. 4 and 7. Drive tool 88 includes a handle 90 (shown in phantom in FIG. 4) and a driver 92 coupled to handle 90. Driver 92 includes a handle portion 94, a screw-receiving portion 96 positioned to lie in spaced-apart relation to handle portion 94, and an elongated shaft portion 98 extending between handle portion 94 and screw-receiving portion 96. As best seen in FIG. 5, driver 92 further includes an outer surface 100 and an inner surface 102 formed to define a cannula 104 therethrough. Cannula 104 is circular in shape and is provided to receive a guidewire 103 during surgery in order to properly align driver 92 within femur 15 and tibia 16, as will be described later.

Still referring to FIG. 4, handle portion 94 of driver 92 is formed to be coupled to handle 90, which may be any type of handle appropriate for use with a drive tool. Shaft portion 98 preferably is elongated and is formed to include a first end 106 coupled to screw-receiving portion 96, a second end 108 coupled to handle portion 94, and a cylindrical wall 110 extending therebetween. Screw-receiving portion 96 includes a first end 112 coupled to first end 106 of shaft portion 98, a second end 114, and a body 116 extending there between. Body 116 forms four outer drive faces 118, as shown in FIG. 5. Body 116 is square-shaped and designed to engage to passageway 30 of screw body 10. However, it is understood that if passageway 30 is formed to have a cross-section shape other than that of a square body, 116 will be formed with a corresponding outer surface with drive faces 118 to engage passageway 30.

Second end 114 of screw-receiving portion 96 forms a tapered portion 120 coupled to drive faces 118 of body 116. A distance (not shown) between opposite outer drive faces 118 of screw-receiving portion 96 is smaller than a diameter (not shown) of shaft portion 98 so that a ridge 122 is formed where first end 112 of screw-receiving portion 96 and first end 106 of shaft portion 98 are coupled to each other, as shown in FIG. 6.

Figure 6:
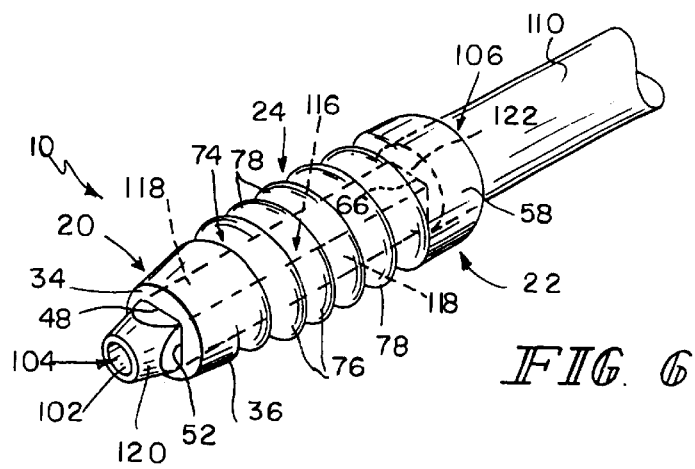
FIG. 6 is a perspective view similar to FIG. 5 showing the body of the screw-receiving portion received within the passageway of the screw body so that the tapered portion of the screw-receiving portion is positioned to extend beyond the tip portion of the screw body.

In operation, screw-receiving portion 96 is received within passageway 30 of screw body 10, as shown in FIG. 6, so that rear face 56 abuts ridge 122 and tapered portion 120 extends beyond front face 34 to provide a tapered front end to aid in insertion. Body 116 is positioned to lie within passageway 30 so that each outer drive face 118 of body 116 faces each inner drive face 32 of screw body 10. Because passageway 30 extends through the entire screw body 10, the outer drive faces 118 distribute the driving force of drive tool 88 along the entire length L of screw body 10 while screw body 10 is being drilled into bone 13.

To explain further, drive tool 88 transfers torque to screw body 10 throughout the entire length L of passageway 30 because drive tool 88 extends completely through screw body 10. Bending and rotational forces produced by drive tool 88 are equally distributed by outer drive faces 118 of drive tool 88 to inner drive faces 32 of screw body 10 and across the entire axial length L of screw body 10. Thus, stresses are not focused onto any discrete area of screw body 10 and the chance of fracture or breakage of screw body 10 is thereby minimized. In a preferred embodiment, drive tool 88 is made of stainless steel or another strong material suitable for a surgical setting while screw body 10 is made of a biodegradable material.

Referring now to FIG. 7, an ACL reconstruction is illustrated, for example, where two screw bodies 10 are used to secure soft tissue graft 12 to femur 14 and tibia 16. First, a tibial tunnel 124 is drilled through tibia 16 and a femoral tunnel 126 is drilled into femur 14. Soft tissue graft 12 is then guided through tibial tunnel 124 and femoral tunnel 126. Once soft tissue graft 12 is properly inserted and is tensioned both proximally and distally within tibial and femoral tunnels 124, 126, a first screw body 10 may be inserted through tibial tunnel 124 and into femoral tunnel 126 by using drive tool 88 in order to wedge screw body 10 between soft tissue graft 12 and bone 13 of femur 14. Optionally, driver 92 of drive tool 88 receives guidewire 103 through cannula 104 in order to guide driver 92, and screw body 10 mounted thereon, within tibial and femoral tunnels 124, 126. Next, a second screw body 10 may be inserted into tibial tunnel 124 by using the same method in order to secure soft tissue graft 12 to tibia 16.

For the insertion of screw body 10 within tibial and femoral tunnels 124, 126, screw body 10 is placed on screw-receiving portion 96 so that tapered portion 120 of screw-receiving portion 96 is positioned to extend out from front face 34 of screw body 10. Ridge 122 provides a means to hold and balance screw body 10 on driver 92 so that screw body 10 does not slide along shaft portion 98. Driver 92 is then rotated, as shown by arrow 130 in FIG. 7, in order to drill screw body 10 into tibial and femoral tunnels 124, 126. As mentioned before, crests 78 of threaded portion 24 of screw body 10 are preferably rounded in order to engage bone 13 while not damaging soft tissue graft 12. Once bone screw 10 is securely fit within either of the tibial and femoral tunnels 124, 126, driver 92 is withdrawn from within passageway 30 of screw body 10. Screw bodies 10 are then left within tibial and femoral tunnels 124, 126 to eventually be absorbed by the patient's body.

Although the invention has been described in detail with reference to certain preferred embodiments, variations and modifications exist within the scope and spirit of the invention as described and defined in the following claims.

What is claimed is:

1. A screw comprising
a screw body having a tip portion formed to include a front face,
an end portion formed to include a rear face,
a threaded portion adjacent to and positioned to lie between the tip portion and the end portion,
the threaded portion comprising a thread formed to include alternating crests and troughs, wherein the crests are rounded, and
a passageway extending from the front face of the tip portion to the rear face of the end portion, the passageway being formed by drive faces extending from the front face of the tip portion to the rear face of the end portion.

2. The screw of claim 1 wherein the screw body is comprised of a bioabsorbable material.

3. The screw of claim 1 wherein the passageway has a polygonal cross-section and the polygonal cross-section is constant from the front face of the tip portion to the rear face of the end portion.

4. The screw of claim 3 wherein the polygonal cross-section is square.

5. The screw of claim 1 wherein the tip portion further includes a frustoconically shaped outer wall and having a first end adjacent to the front face and a second end adjacent to the threaded portion, wherein the first end has a diameter less than a diameter of the second end.

6. The screw of claim 1 wherein the thread forms thread segments and each thread segment is formed to include one crest and the troughs are formed between each crest.

7. The screw of claim 1 wherein the troughs are rounded.

8. The screw of claim 1, wherein the front face includes a front opening of the passageway having a width W and a length L and the rear face includes a rear opening of the passageway having a width W' equal to width W of the front opening and a length L' equal to length L of the front opening.

9. The screw of claim 1, wherein the end portion further includes an outer cylindrical wall having a first end adjacent to the threaded portion, a second end adjacent to the rear face, and rear edges having a rounded shape and being formed by the second end and the rear face.

10. The screw of claim 1 wherein the tip portion includes a tapered first end adjacent to the front face.

11. A screw and driver combination,
the driver comprising a screw-receiving portion and a handle portion positioned to lie in spaced-apart relation to the screw-receiver, the screw-receiving portion having a plurality of longitudinally extending driving surfaces, and
the screw comprising a screw body having a tip portion formed to include a front face, an end portion formed to include a rear face, a threaded portion formed to extend between the tip portion and the end portion and including a thread having rounded crests, and a plurality of drive faces formed to define a passageway such that the drive faces and passageway extend through an entire length of the screw body from the front face of the tip portion to the rear face of the end portion, the passageway of the screw formed to receive the screw-receiving portion therein so that the drive faces of the screw body conformingly engage the driving surfaces of the driver throughout the entire length of the screw body.

12. The screw and driver combination of claim 11 wherein the driver further comprises a shaft extending between the screw-receiving portion and the handle, a ridge is provided between the shaft and the screw-receiving portion, and the screw-receiving portion is provided with a tip, whereby when the screw-receiving portion is received within the passageway of the screw body, the rear face of the screw body abuts the ridge of the driver and the tip of the driver extends beyond the front face of the screw body.

13. The screw and driver combination of claim 12, wherein the tip of the screw-receiving portion is tapered.

14. The screw and driver combination of claim 12, wherein the driver further includes a cannula extending from the tip to the handle.

15. The screw and driver combination of claim 11, wherein the screw-receiving portion includes four driving surfaces defining a square cross-section and a cross-section of the passageway is a corresponding square.

16. The screw and driver combination of claim 11 wherein the screw is comprised of a biodegradable material.

17. A bioabsorbable screw comprising
  a screw body including a tip portion having a front face, an end portion having a rear face and being positioned to lie in spaced-apart relation to the tip portion, a threaded portion having a rounded thread extending between the tip portion and the end portion, and a passageway extending the length of the screw body from the front face to the rear face and having a square-shaped cross-section which remains uniform along the length of the screw body.

18. The bioabsorbable screw of claim 17 wherein the threaded portion is formed to include a single thread having multiple thread segments and forming crests and troughs, wherein each crest and trough is rounded in shape.

19. A method of fixing a tissue graft within a bone tunnel comprising the steps of:
  preparing the bone tunnel to receive the graft,
  inserting the tissue graft into the bone tunnel,
  providing a screw having a thread, the thread including rounded crests, and having an axial passageway, the passageway including a plurality of longitudinally extending drive faces extending the entire length of the screw from the front face to the rear face, and
  driving the screw into the bone tunnel by applying a driving force along the entire length of each of the drive faces.

20. The method of claim 19 wherein the passageway has a polygonal cross-section extending along the length of the screw.

21. The method of claim 19 wherein the polygonal cross-section is square, defining four drive faces.

22. The method of claim 19 wherein the screw is comprised of bioabsorbable material.

23. The method of claim 19 wherein the driving step includes using a driver having a driving portion formed to be received within the passageway and to engage each of the drive faces along the entire length of the screw.

24. The method of claim 23 wherein the driving portion has a plurality of driving surfaces for engaging the drive faces in a face-to-face relationship.

\* \* \* \* \*